(12) United States Patent
Weber et al.

(10) Patent No.: US 6,291,491 B1
(45) Date of Patent: Sep. 18, 2001

(54) AMIDE DERIVATIVES AS β 3 AGONISTS

(75) Inventors: Ann E. Weber; Emma R. Parmee, both of Scotch Plains; Robert Mathvink, Red Bank; Wallace T. Ashton, Edison, all of NJ (US); Elizabeth M. Naylor, Harlow (GB)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/689,169

(22) Filed: Oct. 12, 2000

Related U.S. Application Data

(60) Provisional application No. 60/158,871, filed on Oct. 12, 1999.

(51) Int. Cl.$^7$ .................. C07D 213/56; C07D 213/61; A61K 31/44
(52) U.S. Cl. ............. 514/357; 514/255.02; 514/332; 514/342; 514/352; 514/365; 514/617; 544/405; 546/265; 546/270.7; 546/309; 546/336; 548/194; 564/182
(58) Field of Search ................. 514/255.02, 332, 514/342, 352, 357, 365, 617; 544/405; 546/265, 270.7, 309, 336; 548/194; 564/182

(56) References Cited

FOREIGN PATENT DOCUMENTS

WO 99/20607 A1   4/1999  (WO) .

OTHER PUBLICATIONS

Chemical Abstract No. 129:198012d (JP 10–218861) 1998.

*Primary Examiner*—Zinna Northington Davis
(74) *Attorney, Agent, or Firm*—Mollie M. Yang; David L. Rose

(57) ABSTRACT

Amide derivatives are selective $\beta_3$ adrenergic receptor agonists with very little $\beta_1$ and $\beta_2$ adrenergic receptor activity and as such the compounds are capable of increasing lipolysis and energy expenditure in cells. The compounds thus have potent activity in the treatment of Type II diabetes and obesity. The compounds can also be used to lower triglyceride levels and cholesterol levels or raise high density lipoprotein levels or to decrease gut motility. In addition, the compounds can be used to reduced neurogenic inflammation or as antidepressant agents. Compositions and methods for the use of the compounds in the treatment of diabetes and obesity and for lowering triglyceride levels and cholesterol levels or raising high density lipoprotein levels or for increasing gut motility are also disclosed.

18 Claims, No Drawings

AMIDE DERIVATIVES AS β 3 AGONISTS

CROSS-REFERENCE TO RELATED APPLICATIONS

This application is a non-provisional application related to U.S. application Ser. No. 60/158,871 filed on Oct. 12, 1999 priority of which is claimed hereunder.

SUMMARY OF THE INVENTION

The instant invention is concerned with amide derivatives which are useful as antiobesity and antidiabetic compounds. Thus, it is an object of this invention to describe such compounds. It is a further object to describe the specific preferred stereoisomers of the present compounds. A still further object is to describe processes for the preparation of such compounds. Another object is to describe methods and compositions which use the compounds as the active ingredient thereof. Further objects will become apparent from reading the following description.

BACKGROUND OF THE INVENTION

β-Adrenoceptors have been subclassified as $β_1$ and $β_2$ since 1967. Increased heart rate is the primary consequence of $β_1$-receptor stimulation, while bronchodilation and smooth muscle relaxation typically result from $β_2$ stimulation. Adipocyte lipolysis was initially thought to be solely a $β_1$-mediated process. However, more recent results indicate that the receptor mediating lipolysis is atypical in nature. These atypical receptors, later called $β_3$-adrenoceptors, are found on the cell surface of both white and brown adipocytes where their stimulation promotes both lipolysis (breakdown of fat) and energy expenditure.

Early developments in this area produced compounds with greater agonist activity for the stimulation of lipolysis ($β_3$ activity) than for stimulation of atrial rate ($β_1$) and tracheal relaxation ($β_2$). These early developments disclosed in Ainsworth et al., U.S. Pat. Nos. 4,478,849 and 4,396,627, were derivatives of phenylethanolamines.

Such selectivity for $β_3$-adrenoceptors could make compounds of this type potentially useful as antiobesity agents. In addition, these compounds have been reported to show antihyperglycemic effects in-animal models of non-insulin-dependent diabetes mellitus.

A major drawback in treatment of chronic diseases with $β_3$ agonists is the potential for stimulation of other β-receptors and subsequent side effects. The most likely of these include muscle tremor ($β_2$) and increased heart rate ($β_1$). Although these phenylethanolamine derivatives do possess some $β_3$ selectivity, side effects of this type have been observed in human volunteers. It is reasonable to expect that these side effects resulted from partial $β_1$ and/or $β_2$ agonism.

More recent developments in this area are disclosed in Ainsworth et al., U.S. Pat. No. 5,153,210, Caulkett et al, U.S. Pat. No. 4,999,377, Alig et al., U.S. Pat. No. 5,017,619, Lecount et al., European Patent 427480 and Bloom et al., European Patent 455006.

Even though these more recent developments purport to describe compounds with greater $β_3$ selectivity over the $β_1$ and $β_2$ activities, this selectivity was determined using rodents, in particular, rats as the test animal. Because even the most highly selective compounds, as determined by these assays, still show signs of side effects due to residual $β_1$ and $β_2$ agonist activity when the compounds are tested in humans, it has become apparent that the rodent is not a good model for predicting human $β_3$ selectivity.

Recently, assays have been developed which more accurately predict the effects that can be expected in humans. These assays utilize cloned human $β_3$ receptors which have been expressed in Chinese hamster ovary cells. See Emorine et al, *Science*, 1989, 245:1118–1121; and Liggett, *Mol. Pharmacol.*, 1992, 42:634–637; and Grannemann et al., *Mol. Pharmacol.*, 1992,42: 964–970. The agonist and antagonist effects of the various compounds on the cultivated cells provide an indication of the antiobesity and antidiabetic effects of the compounds in humans.

U.S. Pat. No. 5,451,677 discloses selective $β_3$ agonists of the formula:

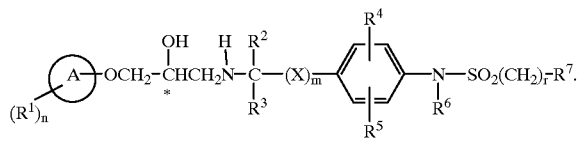

PCT Application WO95/29159 published Nov. 2, 1995 discloses selective $β_3$ agonists of the formula

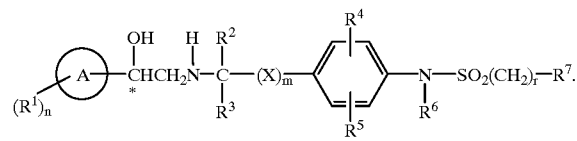

PCT Application WO99/20607 disclosed β3 agonists of the formula

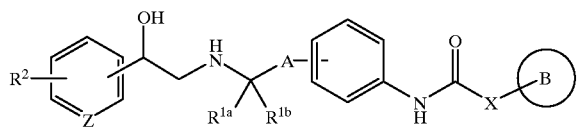

Japanese Kokai 10218861 discloses β3 agonists of the formula

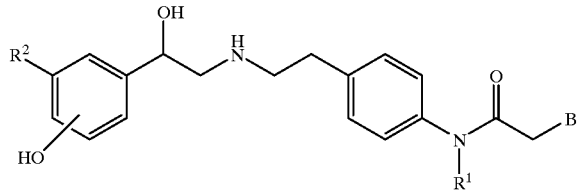

DETAILED DESCRIPTION OF THE INVENTION

The present invention provides compounds of the formula I:

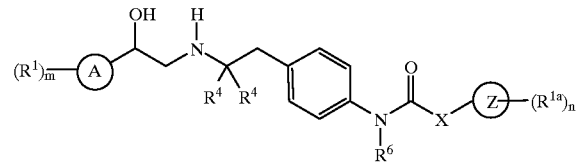

wherein m is 0 to 5;

n is 0 to 5;

p is 0, 1 or 2;

A is
- (1) benzene,
- (2) a 5 or 6-membered heterocyclic ring with from 1 to 4 heteroatoms selected from oxygen, sulfur and nitrogen,
- (3) a benzene ring fused to a 5 or 6-membered heterocyclic ring with from 1 to 4 heteroatoms selected from oxygen, sulfur and nitrogen, or
- (4) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen;

X is
- (1) $C_1$–$C_3$ alkylene,
- (2) $C_1$–$C_3$ alkylene wherein said alkylene contains Q.
- (3) $NR^6$,
- (4) O, or
- (5) a bond;
  with the proviso that when $R^6$ is H, Z is heteroaryl and X is $C_1$–$C_3$ alkylene, NH, or a bond, the moiety $(R^1)$m-A is not phenyl, pyridyl, phenyl monosubstituted with halogen or pyridyl monosubstituted with halogen; with the further proviso that when Z is pyridyl, oxazolyl, thiazolyl or imidazolyl, X is methylene, and A is phenyl, then $R^1$ attached to A is not hydroxy;

Z is
- (1) phenyl,
- (2) naphthyl,
- (3) a 5 or 6-membered heterocyclic ring with from 1 to 4 heteroatoms selected from oxygen, sulfur and nitrogen,
- (4) a benzene ring fused to a $C_5$–$C_{10}$ carbocyclic ring,
- (5) a benzene ring fused to a 5 or 6-membered heterocyclic ring with from 1 to 4 heteroatoms selected from oxygen, sulfur and nitrogen,
- (6) a 5 or 6membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen, or
- (7) a 5 or 6-membered heterocyclic ring with from 1 to 4 heteroatoms selected from oxygen, sulfur and nitrogen fused to a $C_5$–$C_{10}$ carbocyclic ring;

$R^1$ is
- (1) $C_1$–$C_{10}$ alkyl optionally substituted with up to 5 groups selected from
  - (a) hydroxy,
  - (b) halogen,
  - (c) cyano,
  - (d) $QR^2$,
  - (e) $C_3$–$C_8$ cycloalkyl,
  - (f) Z optionally substituted with up to 5 groups selected from halogen, $R^2$, $QR^2$, oxo, and $CO_2R^2$
  - (g) $Q'COR^3$,
  - (h) $S(O)_pNR^2R^2$,
  - (i) $NR^2SO_2R^3$, and
  - (j) $Q'CO_2R^2$;
- (2) $C_3$–$C_8$ cycloalkyl,
- (3) oxo,
- (4) halogen,
- (5) cyano,
- (6) $QR^2$,
- (7) $S(O)_pNR^2$,
- (8) $Q'COR^3$,
- (9) $NR^2SO_2R^3$,
- (10) $Q'CO_2R^2$, or
- (11) Z optionally substituted with up to 5 groups independently selected from
  - (a) $R^2$,
  - (b) $QR^2$,
  - (c) halogen, and
  - (d) oxo;

$R^{1a}$ is
- (1) a group selected from $R^1$, or
- (2) Z optionally substituted with up to 5 groups selected from $R^1$;

$R^2$ is
- (1) hydrogen,
- (2) $C_1$–$C_{10}$ alkyl optionally substituted with up to 5 groups selected from
  - (a) hydroxy,
  - (b) halogen,
  - (c) $CO_2R^4$,
  - (d) $S(O)_p$—$C_1$–$C_{10}$ alkyl,
  - (e) $C_3$–$C_8$ cycloalkyl,
  - (f) $C_1$–$C_{10}$ alkoxy optionally substituted with up to 5 halogens, and
  - (g) Z optionally substituted with up to 5 groups selected from halogen, trifluoromethyl, trifluoromethoxy, $C_1$–$C_{10}$ alkyl and $C_1$–$C_{10}$ alkoxy,
- (3) $C_3$–$C_8$ cycloalkyl, or
- (4) Z optionally substituted with up to 5 groups selected from
  - (a) halogen,
  - (b) nitro,
  - (c) oxo,
  - (d) $NR^4R^4$,
  - (e) $C_1$–$C_{10}$ alkoxy optionally substituted with up to 5 halogens,
  - (f) $S(O)_p$—$C_1$–$C_{10}$ alkyl, and
  - (g) $C_1$–$C_{10}$ alkyl optionally substituted with up to 5 groups selected from hydroxy, halogen, trifluoromethyl, cyano, $CO_2R^4$, $C_3$–$C_8$ cycloalkyl, and $QR^5$;

$R^3$ is
- (1) $R^2$ or
- (2) $NR^2R^2$;

$R^4$ is
- (1) H, or
- (2) $C_1$–$C_{10}$ alkyl;

$R^5$ is
- (1) Z optionally substituted with up to 5 groups selected from halogen, trifluoromethyl, cyano, $C_1$–$C_{10}$ alkyl and $C_1$–$C_{10}$ alkoxy, or
- (2) $C_1$–$C_{10}$ alkyl;

$R^6$ is
- (1) H or
- (2) $C_1$–$C_{10}$ alkyl, or when X is $NR^6$ the two R6 groups together complete a 5- or 6-membered ring;

Q is
- (1) $N(R^2)$,
- (2) O or
- (3) $S(O)_p$;

Q' is
- (1) N(R$^2$),
- (2) O or
- (3) a bond; or a pharmaceutically acceptable salt thereof.

In one subset of formula I are compounds wherein
A is
- (1) a 5- or 6-membered heterocyclic ring with from 1 to 4 heteroatoms selected from oxygen, sulfur and nitrogen, other than pyridyl,
- (2) a benzene ring fused to a 5 or 6-membered heterocyclic ring with from 1 to 4 heteroatoms selected from oxygen, sulfur and nitrogen, or
- (3) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen.

In another subset of formula I are compounds wherein R$^4$ and R$^6$ are each hydrogen.

In another subset of formula I are compounds of formula Ia:

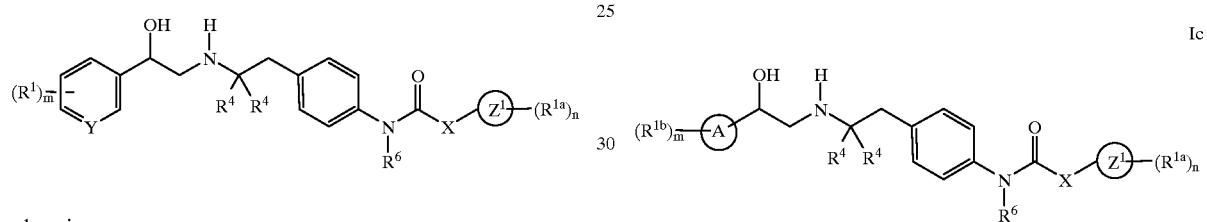

wherein
- m is 0 or 1;
- Y is CH or N;
- R$^1$ is halogen;
- Z$^1$ is
  - (1) phenyl,
  - (2) naphthyl,
  - (3) a benzene ring fused to a C$_5$–C$_{10}$ carbocyclic ring.

In another subset of formula I are compounds of formula Ib:

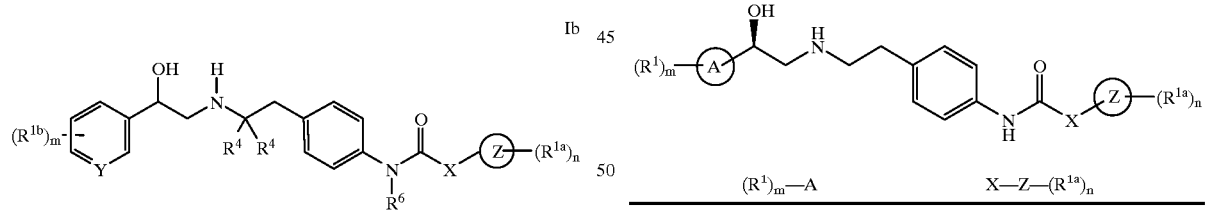

wherein
- m is 1 to 3;
- Y is CH or N;
- R$^{1b}$ is
  - (1) C$_1$–C$_{10}$ alkyl optionally substituted with up to 5 groups selected from
    - (a) hydroxy,
    - (b) halogen,
    - (c) cyano,
    - (d) QR$^2$,
    - (e) C$_3$–C$_8$ cycloalkyl,
    - (f) Z optionally substituted with up to 5 groups selected from halogen, R$^2$, QR$^2$, oxo, and CO$_2$R$^2$
    - (g) Q'COR$^3$,
    - (h) S(O)$_p$NR$^2$R$^2$,
    - (i) NR$^2$SO$_2$R$^3$, and
    - (j) Q'CO$_2$R$^2$;
  - (2) C$_3$–C$_8$ cycloalkyl,
  - (3) cyano,
  - (4) QR$^2$,
  - (5) S(O)$_p$NR$^2$R$^2$,
  - (6) Q'COR$^3$,
  - (7) NR$^2$SO$_2$R$^3$,
  - (8) Q'CO$_2$R$^2$, or
  - (9) Z optionally substituted with up to 5 groups independently selected from
    - (a) R$^2$,
    - (b) QR$^2$,
    - (c) halogen, and
    - (d) oxo.

In a preferred subset are compounds of formula Ib wherein
- m is 1, and
- R$^{1b}$ is cyano or QR$^2$.

In another preferred subset are compounds of formula Ib wherein Z is selected from the group consisting of phenyl, pyridyl, and thiazolyl.

In another subset of formula I are compounds of formula Ic:

Ic (R$^{1b}$)$_m$—A—CH(OH)—CH$_2$—NH—C(R$^4$)(R$^4$)—CH$_2$—[phenyl]—N(R$^6$)—C(O)—X—Z$^1$—(R$^{1a}$)$_n$ wherein
Z$^1$ is
- (1) phenyl,
- (2) naphthyl,
- (4) a benzene ring fused to a C$_5$–C$_{10}$ carbocyclic ring.

Representative compounds of formula I are as follows:

| (R$^1$)$_m$—A | X—Z—(R$^{1a}$)$_n$ |
|---|---|
| 6-cyano-2-pyridyl | 2-amino-4-thiazolylmethyl |
| 6-cyano-2-pyridyl | 2-pyridylmethyl |
| 3-pyridazinyl | 2-amino-4-thiazolylmethyl |
| 3-methyl-5-isoxazolyl | 2-amino-4-thiazolylmethyl |
| 3-cyanophenyl | 2-pyridylmethyl |
| 3-cyanophenyl | 2-amino-4-thiazolylmethyl |
| 2-methyl-3-pyridyl | 2-pyridylmethyl |
| 2-methyl-3-pyridyl | 2-amino-4-thiazolylmethyl |
| 3-pyridyl | 4-aminophenylmethyl |
| 6-amino-3-pyridyl | 2-amino-4-thiazolylmethyl |
| 6-amino-3-pyridyl | 2-pyridylmethyl |
| 6-amino-3-pyridyl | 2-pyridylmethyloxy |

Throughout the instant application, the following terms have the indicated meanings:

"Alkylene" means —(CH$_2$)$_q$— where q is the designated carbon number; one or two of the hydrogen may be optionally replaced by methyl or halogen.

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atoms fluorine, chlorine, bromine and iodine.

The term "carbocyclic ring" is intended to include both aromatic and nonaromatic rings containing only carbon atoms. Thus, a benzene ring fused to a $C_5-C_{10}$ carbocyclic ring, includes naphthyl, tetrahydronaphthyl, indanyl and indenyl. A 5 or 6-membered heterocyclic ring with from 1 to 4 heteroatoms selected from oxygen, sulfur and nitrogen fused to a $C_5-C_{10}$ carbocyclic ring includes benzene fused to a heterocyclic ring as well as a non-aromatic carbocyclic ring fused to a heterocyclic ring. The carbocyclic ring preferably is $C_5-C_7$.

A 5 and 6-membered heterocyclic ring, whether isolated or as a part of a fused ring system, is intended to include aromatic and non-aromatic heterocycles; and where the heterocycle is part of a fused ring, at least one of the rings is aromatic. Examples of a 5 or 6-membered ring include pyridyl, pyrimidinyl, pyrrolyl, furyl, thienyl, imidazolyl, thiazolyl, thiadiazolyl, tetrazolyl, oxadiazolyl, oxazolyl, imidazolidinyl, pyrazolyl, isoxazolyl. Examples of a benzene ring fused to a 5 or 6-membered heterocyclic ring include benzothiadiazolyl, indolyl, indolinyl, benzodioxolyl, benzodioxanyl, benzothiophenyl, benzofuranyl, benzimidazolyl, benzoxazinyl, benzisoxazolyl, benzothiazolyl, 2,3-dihydrobenzofuranyl, quinolinyl, benzotriazolyl, benzoxazolyl, 1,2,3,4-tetrahydroisoquinolinyl, 1,2,3,4-tetrahydroquinolinyl. Examples of a 5 or 6membered heterocyclic ring fused to a 5 or 6-membered heterocyclic ring include purinyl, furopyridine and thienopyridine. Examples of a 5 or 6-membered heterocyclic ring fused to a non-aromatic carbocyclic ring include tetrahydrobenzothiazolyl, 5,6,7,8-tetrahydroquinolinyl, 2,3-cyclopentenopyridyl, 4,5,6,7-tetrahydroindolyl, 5,6,7,8-tetrahydroisoquinolyl, 5,6,7,8-tetrahydroquinoxalinyl.

"Heteroaryl" is a mono-or bicyclic aromatic ring containing from 1 to 6 heteroatoms independently selected from N, O and S wherein each ring has five or six ring atoms.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Throughout the instant application, when reference is made to "compounds of Formula I" it is meant to include, unless otherwise specified, pharmaceutically acceptable salts and prodrugs thereof. Prodrugs are derivatives of compounds of Formula I that are transformed in vivo to the active drug molecule; prodrugs include derivatives of free hydroxy, amino or carboxylic groups such as esters, ethers, amides, carbonates, carbamates, and N-alkyl derivatives. Specific examples of prodrugs of compounds of Formula I include-derivation of the secondary amine such as N-alkylation (methyl, ethyl, isopropyl and 2-methoxyethyl), and N-acylation (1-pyrrolidinylacetyl, 4morpholinylacetyl, (1-acetoxy)ethoxycarbonyl, and dimethylaminoacetyl). Prodrugs of the above-described types may be readily prepared from compounds of Formula I using methods well known to persons skilled in the art.

Certain of the above defined terms may occur more than once in the above formula and upon such occurrence each term shall be defined independently of the other, thus for example, $NR^2R^2$ may represent $NH_2$, $NHCH_3$, $N(CH_3)CH_2CH_3$, and the like.

The compounds (I) of the present invention can be prepared as described in the following schemes. As illustrated in Scheme 1, amine 1 is coupled with acid 2 (Y=OH, X=alkyl or bond) in the presence of a peptide coupling reagent such as EDC/HOBt and a base such as diisopropylethylamine or triethylamine to provide Boc-protected intermediate 3 (X=alkyl or bond). Alternatively, amine 1 is treated with acid chloride 2 (Y=Cl, X=alkyl or bond), chloroformate 2 (Y=Cl, X=O), or carbamoyl chloride 2 (Y=Cl, X=$NR^6$) in the presence of a base such as diisopropylethylamine or triethylamine to provide 3. Deprotection of the Boc group by treatment with an acid such as trifluoroacetic acid in dichloromethane or hydrogen chloride in diethyl ether gives the desired product (1).

SCHEME 1

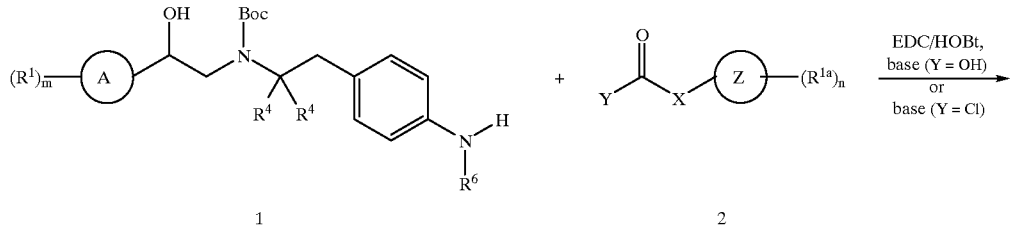

-continued

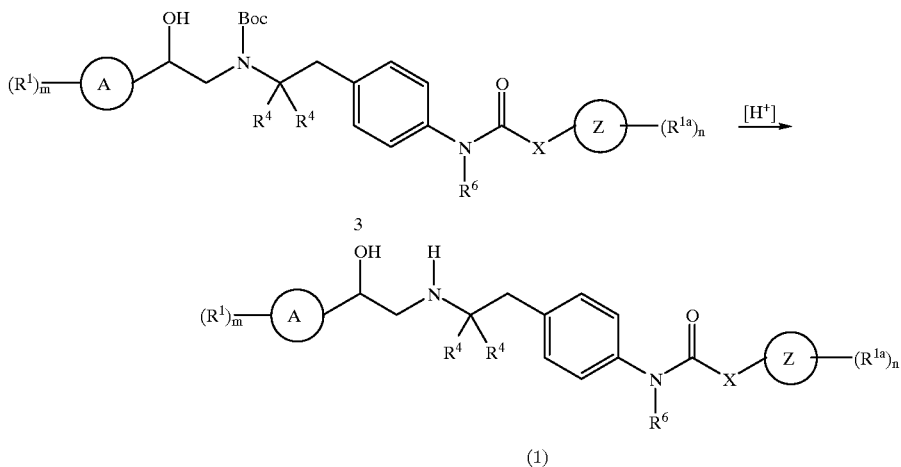

Intermediate 3 where X is NH may be prepared as shown in Scheme 2. Amine 1 is treated with isocyanate 4 to provide intermediate 3.

SCHEME 2

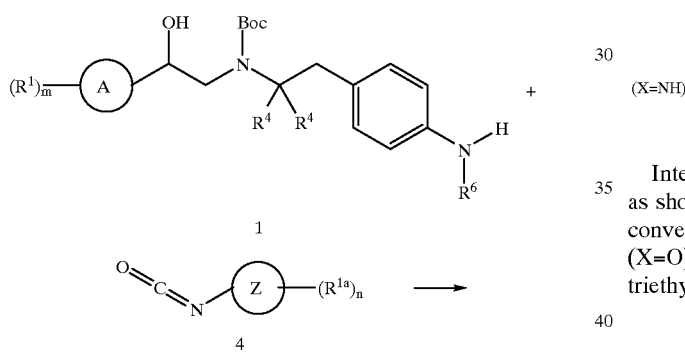

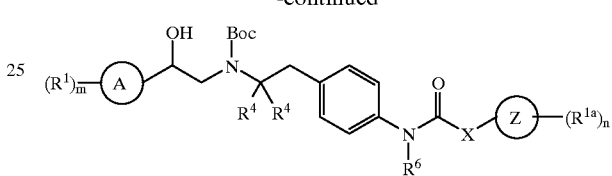

(X=NH)

Intermediate 3 where X is O or NR$^6$ may also be prepared as shown in Scheme 3. Amine 1 is treated with phosgene, conveniently as a solution in toluene, and then alcohol 5 (X=O) or amine 5 (X=NR$^6$) in the presence of base such as triethylamine to provide intermediate 3 (X=O or NR$^6$).

SCHEME 3

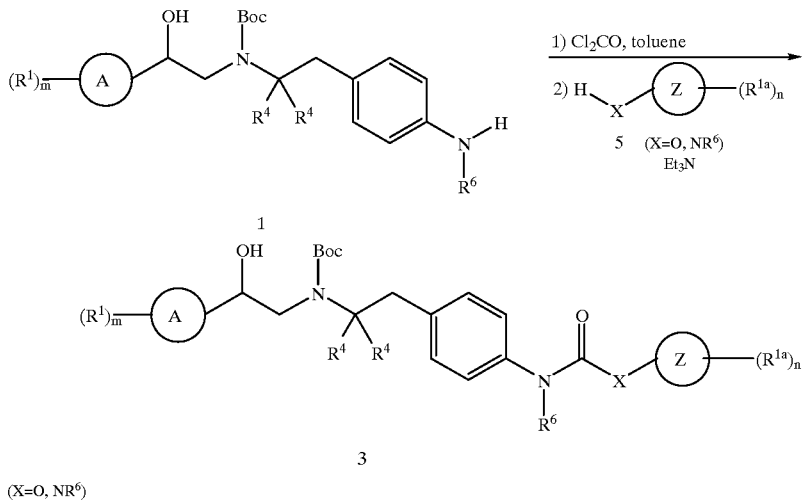

(X=O, NR$^6$)

Intermediates 2 isocyantes 4, intermediates 5 are commercially available, known in the literature, or may be prepared by methods commonly known to those skilled in the art. Amines 1 where $R^6$ is H are known in the literature (see for example, Fisher, et al., U.S. Pat. No. 5,561,142 (1996) and Fisher, et al., U.S. Pat. No. 5,705,515 (1998), or may be prepared by methods commonly known to those skilled in the art.

Amines 1 where $R^6$ is alkyl may be prepared from the corresponding amine where $R^6$ is H by methods commonly known to those skilled in the art. One convenient method for $R^6$=alkyl shown in Scheme 4 involves the treatment of amine 1 ($R^6$=H) with aldehyde 6 and sodium triacetoxyborohydride to provide the corresponding amine 1 ($R^6$= alkyl).

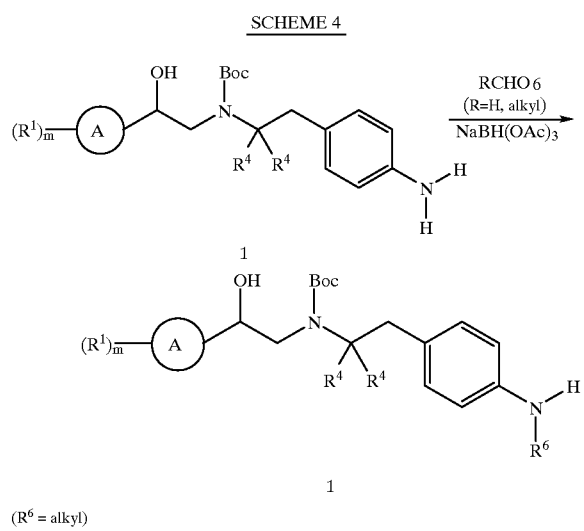

SCHEME 4

In some cases, the products from the reactions described in Schemes 1 to 4 may be further modified, for example, by the removal of protecting groups or the manipulation of substituents on $R^1$ and/or $R^{1a}$. These manipulations may include, but are not limited to, reduction, oxidation, alkylation, acylation, and hydrolysis reactions, which are commonly known to those skilled in the art.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, fumaric, hydrobromic, hydrochloric, maleic, phosphoric, sulfuric, trifluoroacetic, and tartaric acids.

It will be understood that, as used herein, references to the compounds of Formula I are meant to also include the pharmaceutically acceptable salts.

Utilities

Compounds of the present invention are potent agonists of the β3-adrenoceptor, and as such are useful in treating or preventing diseases, disorders or conditions mediated by the activation of β3-adrenoceptor. Thus one aspect of the present invention provides a method for the treatment, control or prevention of such diseases, disorders, or conditions in a mammal which comprises administering to such mammal a therapeuticallyeffective amount of a compound of Formula I. The term "mammal" includes human and non-human animals such as dogs and cats and the like. The diseases, disorders or conditions for which compounds of the present invention are useful in treating or preventing include, but are not limited to, (1) diabetes mellitus, (2) hyperglycemia, (3) obesity, (4) hyperlipidemia, (5) hypertriglyceridemia, (6) hypercholesterolemia, (7) atherosclerosis of coronary, cerebrovascular and peripheral arteries, (8) gastrointestinal disorders including peptid ulcer, esophagitis, gastritis and duodenitis, (including that induced by H. pylori), intestinal ulcerations (including inflammatory bowel disease, ulcerative colitis, Crohn's disease and proctitis) and gastrointestinal ulcerations, (9) neurogenic inflammation of airways, including cough, asthma, (10) depression, (11) prostate diseases such as benign prostate hyperplasia, (12) irritable bowel syndrome and other disorders needing decreased gut motility, (13) diabetic retinopathy, (14) neuropathic bladder dysfunction, and (15) elevated intraocular pressure and glaucoma.

Administration and Dose Ranges

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 3500 milligrams. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical unit dosage form containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;
(b) insulin or insulin mimetics;
(c) sulfonylureas such as tolbutamide and glipizide;
(d) α-glucosidase inhibitors (such as acarbose),
(e) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor α agonists such as fenofibric acid derivatives (gemfibrozil, clofibrat, fenofibrate and benzafibrate), (iv) inhibitors of cholesterol absorption for example beta-sitosterol and (acyl CoA:cholesterol acyltransferase) inhibitors for example melinamide, (v) probucol, (vi) vitamin E, and (vii) thyromimetics;
(f) PPARδ agonists such as those disclosed in WO97/28149;
(g) antiobesity compounds such as fenfluramine, dexfenfluramine, phentermine, sibutramine, orlistat, and other $β_3$ adrenergic receptor agonists;
(h) feeding behavior modifying agents such as neuropeptide Y antagonists (e.g. neuropeptide Y5) such as those disclosed in WO 97/19682, WO 97/20820, WO 97/20821, WO 97/20822 and WO 97120823;
(i) PPARα agonists such as described in WO 97/36579 by Glaxo;
(j) PPARγ antagonists as described in WO97/10813; and
(k) serotonin reuptake inhibitors such as fluoxetine and sertraline.

Biological Assays

The following in vitro assays are suitable for screening compounds that have selective β3 agonist activity:

Functional Assay: cAMP production in response to ligand is measured according to Barton et al (1991, Agonist-induced desensitization of D2 dopamine receptors in human Y-79 retinoblastoma cells. Mol. Pharmacol. v3229:650–658) modified as follows. Chinese hamster ovary (CHO) cells, stably transfected with the cloned β-adrenergic receptor ($β_1$, $β_2$ or $β_3$) are harvested after 3 days of subculturing. Harvesting is done with Enzyme-free Dissociation Media (Specialty Media). Cells are counted and distributed in the assay tubes, after being resuspended in Tris buffer (ACC buffer: 75 mM Tris, pH 7.4, 250 mM Sucrose, 12.5 mM $MgCl_2$, 1.5 mM EDTA, 0.2 mM Sodium Metabisulfite, 0.6 mM IBMX) containing an antioxidant and a phosphodiesterase inhibitor. Reaction is initiated by mixing 200,000 cells in 100 μL with 20 μL of a 6x stock of ligand/unknown to be tested. Tubes shake at 275 rpm for 45 min at room temperature. The reaction is stopped by boiling the tubes for 3 min. The cell lysate is diluted 5-fold in 0.1 N HCl and then acetylated by the mixture of 150 μL of acid-diluted sample with 6 μL of acetylation mixture (acetic anhydride/triethylamine, 1:2.5). The cAMP produced in response to the ligand is measured in the lysate by competing against $^{125}$I-cAMP for binding to a $^{125}$I-cAMP-directed antibody using an automated RIA machine (ATTOFLO, Atto Instruments, Baltimore, Md., Brooker et al 1979, Radioimmunoassay of Cyclic AMP and Cyclic GMP. Advances in Cyclic Nucleotide Research. vol 10: 1–32.). The unknown cAMP level is determined by comparing levels to a standard curve. Alternatively, cAMP is measured using the cAMP SPA kit (code number RPA 556) from Amersham according to the manufacturer's instructions. Samples tested with the latter method do not need to be acetylated.

The non-selective, full agonist β-adrenergic ligand isoproterenol is used at all three receptors to determine maximal stimulation. The human β3 adrenergic receptor (AR) selective ligand (S)-N-[4-[2-[[2-hydroxy-3-(4-hydroxyphenoxy)propyl]amino]ethyl]-phenyl]-4-iodobinzenesulfonamide is used as a control in all assays. Isoproterenol is titrated at a final concentration in the assay of $10^{-10}$ M to $10^{-5}$ M for the β3 AR and $10^{-11}$ M to $10^{-6}$ M for the β1 AR and β2 AR assays. (S)-N-[4-[2-[[2-hydroxy-3-(4-hydroxyphenoxy)propyl]amino] ethyl]phenyl]4-iodobenzenesulfonamide is titrated at the β3 receptor at concentration of $10^{-11}$ M to $10^{-6}$ M. At the β1 AR the concentrations used are $10^{-8}$ M, $10^{-7}$ M, $3 \times 10^{-7}$ M, $10^{-6}$ M, $3 \times 10^{-6}$ M and $10^{-5}$ M. For the β2 AR a single concentration of $10^{-5}$ M is used.

Unknown ligands are initially tested at the β3 AR at a final concentration in the assay of $10^{-7}$ M. Compounds that have an activation at this concentration equal to or greater than 35% of the isoproterenol stimulation are titrated at the β3 AR at concentrations equal to those used to titrate the control (S)-N-[4-[2-[[2-hydroxy-3-(4-hydroxyphenoxy) propyl] amino]ethyl]-phenyl]-4-iodobenzenesulfonamide to determine the $EC_{50}$. The $EC_{50}$ is defined as the concentration of compound that gives 50% activation of its own maximum. Data are analyzed using the Prism program (GraphPan, San Diego, Calif.).

Binding Assay: Compounds are also assayed at the β1 and β2 receptors to determine selectivity. This is done for all compounds using a 6 point binding assay as follows: CHO cells expressing the β1 and the β2 receptors are grown for 3–4 days after splitting. The attached cells are washed with PBS and lysed in 1 mM Tris, pH 7.2 for 10 minutes in ice. The flasks are scraped and the membranes centrifuged at 38,000×g for 15 minutes at 4 ° C. The membranes are resuspended in TME buffer (75 mM Tris, pH 7.4, 12.5 mM $MgCl_2$, 1.5 mM EDTA) at a concentration of 1 mg protein/ml. Large batches of membranes can be prepared, aliquoted and stored at −70° C. for up to a year without loss of potency. The binding assay is performed by incubating together membranes (20–50 μg of protein), the radiolabelled tracer $^{125}$I-cyanopindolol ($^{125}$I-CYP, 45 pM), and the test compounds at final concentrations ranging from $10^{-10}$ M to $10^{-5}$ M in a final volume of 250 μL of TME buffer. The tubes are incubated for 1 hour with shaking at room temperature and the samples are filtered in an IMSCO 96-well cell harvester. The filters are counted in a Gamma counter and the data are analyzed using a 4 parameter fit routine in RS1 (program developed in house using well documented statistical analysis programs) to determine the $IC_{50}$. The $IC_{50}$ is defined as the concentration of the compound capable of inhibiting 50% of the binding of the radiolabelled tracer ($^{125}$I-CYP). A compound's selectivity for the β3 receptor may be determined by calculating the ratio ($IC_{50}$ β1 AR, β2 AR)/($EC_{50}$ β3 AR).

The following examples are provided so that the invention might be more fully understood. They should not be construed as limiting the invention in any way.

EXAMPLE 1

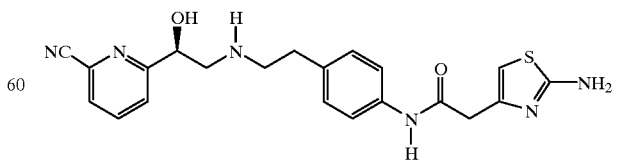

Step A. 2-(2-Chloroacetyl)-6-chloropyridine.

To a mixture of 8.74 g (0.0628 mol) of hydroxypicolinic acid in 13.5 mL (0.145 mol) of phosphorous oxychioride was added 43.2 g (0.207 mol) of phosphorous pentachloride. The mixture was heated at 90° C. for 12 h, cooled to 30° C. and 3.08 mL (0.0816 mol) of formic acid was added dropwise. The excess phosphorous oxychloride was removed in vacuo. Kugelrohr distillation (160° C. @ 0.3 mmHg) afforded 10.69 g (97%) of the corresponding acid chloride.

The acid chloride was dissolved in 50 mL of diethyl ether and the solution cooled to 0° C. Freshly distilled diazomethane (generated from 25 g of Diazald) was added slowly and the resulting yellow solution stirred at room temperature for 3 h. Hydrogen chloride gas was bubbled into the solution for 10 min then the mixture stored at 5° C. overnight. Water was added and the mixture neutralized with solid sodium bicarbonate then extracted three times with diethyl ether. The combined organic phase was washed twice with water, twice with saturated aqueous sodium bicarbonate solution, twice with water, brine, dried over magnesium sulfate and the solvent removed in vacuo to afford 7.12 g (60%) of the title compound as a white solid: $^1$H NMR (300 MHz, CDCl$_3$) δ 8.03 (dd, J=7.6, 0.92 Hz, 1H), 7.86 (t, J=7.8 Hz, 1H), 7.57 (dd, J=8.0, 0.95 Hz, 1H), 5.08 (s, 2H).

Step B. 6-Chloropyridin-2-yloxirane.

To a solution of 10.8 g (33.7 mmol) of (1R)-(-)-B-chlorodiisopinocampheylborane in 5 mL of tetrahydrofuran (THF) cooled to −30° C. was cannulated a pre-cooled solution of 2.91 g (15.3 mmol) of 2-(2-chloroacetyl)-6-chloropyridine in 5 mL of THF. The solution was stirred at −30° C. for 36 h then poured onto ice. The mixture was extracted twice with diethyl ether. The combined organic phase was washed with saturated aqueous sodium bicarbonate solution, brine, dried over magnesium sulfate and the solvent removed in vacuo. Flash chromatography (silica gel, 0 to 20% ethyl acetate-hexanes) afforded 4.06 g of the chlorohydrin as a yellow oil.

To the chlorohydrin in 60 mL of acetone was added 6.34 g (45.9 mmol) of potassium carbonate and 15 mL of water. The mixture was heated at reflux temperature for 9 h then cooled to room temperature. The organic phase was separated and the aqueous phase extracted with diethyl ether. The combined organic phase was dried over magnesium sulfate, the solvent removed in vacuo, and the residue pre-absorbed on florisil. Flash chromatography (silica gel, 0 to 10% ethyl acetate-hexanes) afforded 1.62 g (68%) of the title compound: $^1$H NMR (300 MHz, CDCl$_3$) δ 7.65 (t, J=7.8 Hz, 1H), 7.27 (d, J=7.9 Hz, 1H), 7.16 (d, J=7.6 Hz, 1H), 3.99 (dd, J=4.1, 2.5 Hz, 1H), 3.17 (dd, J=5.7, 4.1 Hz, 1H), 2.88 (dd, J=5.7, 2.5 Hz, 1H).

Step C. (R)-N-[2-(Nitrophenyl)ethyl]-2-hydroxy-2-(6-chloro-2-pyridyl)ethylcarbamic acid 1,1-dimethylethyl ester.

To a solution of 1.37 g (8.81 mmol) of 6-chloropyridin-2-yloxirane in 24 mL of methanol was added a solution of 3.22 g (19.4 mmol) of p-nitrophenethylamine in 24 mL of methanol. The solution was heated at reflux under an atmosphere of nitrogen for 13 h then the solvent removed in vacuo to leave the resultant ethanolamine as a red oil.

To a solution of the ethanolamine in 25 mL of dichloromethane was added 5.77 g (26.4 mmol) of di-tert-butyldicarbonate. The solution was stirred at room temperature overnight then the solvent removed in vacuo. Flash chromatography (silica gel, 20% ethyl acetate-hexanes) afforded 2.56 g (69%) of the title compound as a pale yellow gum.

Step D. (R)-N-[2-(4-Aminophenyl)ethyl]-2-hydroxy-2-(6-cyano-2-pyridyl)ethylcarbamic acid 1,1-dimethylethyl ester.

To a solution of 1.00 g (2.37 mmol) of (R)-N-[2-(4-nitrophenyl)ethyl]-2-hydroxy-2-(6-chloro-2-pyridyl)ethylcarbamic acid 1,1-dimethylethyl ester in 60 mL of methanol under an atmosphere of nitrogen was added 1.35 g (7.12 mmol) of tin(II) chloride. The mixture was heated at reflux for 5 h then cooled to room temperature. Saturated aqueous sodium bicarbonate solution was added followed by ethyl acetate. The resulting emulsion was filtered through Celite and the organic phase separated. The aqueous phase was re-extracted twice with ethyl acetate. The combined organic phase was washed twice with water, brine, dried over magnesium sulfate and the solvent removed in vacuo. Biotage chromatography (40M column, 30, 35% ethyl acetate-hexanes) afforded 510 mg (55%) of (R)-N-[2-(4-aninophenyl)ethyl]-2-hydroxy-2-(6-chloro-2-pyridyl) ethylcarbamic acid 1,1-dimethylethyl ester.

To a solution of 288 mg (0.735 mmol) of (R)-N-[2-(4-aminophenyl)-ethyl]-2-hydroxy-2-(6-chloro-2-pyridyl) ethylcarbamic acid 1,1-dimethylethyl ester in 12 mL of degassed dimethyformamide (DMF) under an atmosphere of nitrogen was added 170 mg (0.147 mmol) of tetrakis (triphenylphosphine)palladium(0) followed by 60.4 mg (0.514 mmol) of zinc cyanide. The mixture was heated at 80° C. for 24 h then 170 mg (0.147 mmol) of tetrakis (triphenylphosphine)palladium(0) was added and the mixture heated at reflux for a further 24 h. After cooling to room temperature, saturated aqueous sodium bicarbonate solution was added and the mixture extracted three times with ethyl acetate. The combined organic phase was washed three times with water, brine, dried over magnesium sulfate and the solvent removed in vacuo. Biotage chromatography (40S column, 50, 60% ethyl acetatehexanes) afforded 217 mg (77%) of the title compound as an off-white foam: $^1$H NMR (400 MHz, CDCl$_3$) δ 7.84 (m, 2H), 7.60 (m, 1H), 6.95 (d, J=7.8 Hz, 2H), 6.65 (m, 2H), 5.33 (s, 1H), 4.97 (s, 1H), 3.60 (m, 4H), 3.36 (m, 1H), 3.23 (m, 1H), 2.70 (m, 2H), 1.46 (s, 9H).

Step E. (R)-N-[4-[2-[[2-Hydroxy-2-(6-cyano-2-pyridyl) ethyl]amino]ethyl]pheny]2-(2-amino4-thiazolyl)acetamide.

To a solution of 25 mg (0.0654 mmol) of (R-N-[2-(4-aminophenyl)ethyl]-2-hydroxy-2-(6-cyano-2-pyridyl) ethylcarbamic acid 1,1-dimethylethyl ester, 12.4 mg (0.0784 mmol) of 2-amino-4-thiazolylacetic acid, and 15.0 mg (0.0782 mmol) of 1-[3-(dimethylamino)propyl]-3-ethylcarbodiimide hydrochloride (EDC), 13.3 mg (0.0984 mmol) of hydroxybenzotriazole (HOBt) in 1.5 mL of DMF under an atmosphere of nitrogen was added 0.028 mL (0.161 mmol) of diethylisopropylamine. The reaction mixture was allowed to stir at room temperature overnight. The mixture was then partitioned between ethyl acetate and water. The aqueous phase was extracted with ethyl acetate and the combined organic phase was washed sequentially with two portions of water and brine, dried over magnesium sulfate, and concentrated in vacuo. Purification by preparative TLC (silica gel, 3% methanol/dichloromethane) afforded 21 mg of BOC protected intermediate. This compound was treated with 2 mL of 1:1 trifluoroacetic acid/dichloromethane at room temperature for 30 min. The solvent was removed in vacuo and the residue purified by preparative TLC (silica gel, 8% (10% ammonium hydroxide in methanol)/dichloromethane) to afford 13 mg (47%) of a pale yellow glass: NMR (400 MHz, CD$_3$OD) δ 7.96 (t, 1H, J=7.9 Hz), 7.79 (d, 1H, J=7.8 Hz), 7.72 (dd, 1H, J=1.0, 7.7 Hz), 7.48 (overlapping d, 2H), 7.15 (d, 2H, J=8.6 Hz), 6.36 (s, 1H), 3.56 (d, 2H, J=0.7 Hz), 3.04–2.78 (m, 6H).

EXAMPLE 2

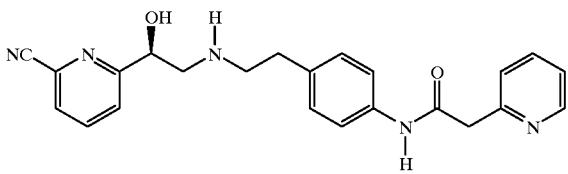

(R)-N-[4-[2-[[2-Hydroxy-2-(6-cyano-2-pridyl)ethyl]amino]ethyl]phenyl]2-(2-pyridyl)acetamide.

Following the procedure outlined in Example 1 the title compound was prepared from 2-(2-pyridyl)acetic acid: NMR (400 MHz, CD$_3$OD) δ 8.50 (m, 1H), 7.96 (t, 1H, J=7.9 Hz), 7.83–7.79 (m, 2H), 7.72 (dd, 1H, J=0.9, 7.6 Hz), 7.50–7.45 (m, 3H), 7.32 (ddd, 1H, J=1.0, 5.0, 7.6 Hz), 7.16 (d, 2H, J=8.6 Hz), 4.83 (m, 1H), 3.90 (s, 2H), 3.02 (dd, 1H, J=4.1, 12.3 Hz), 2.93–2.76 (m, 5H).

EXAMPLE 3

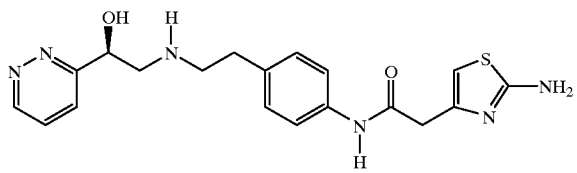

Step A. 3-(2-Bromoacetyl)-6-chloropyridazine.

To a solution of 5.00 g (0.0336 mol) of 3,6-dichloropyridazine in 80 mL of DMF under an atmosphere of nitrogen was added 12.5 mL (0.0370 mol) of tributyl(1-ethoxyvinyl)tin followed by 1.18 g (0.0017 mol) of dichlorobis(triphenylphosphine)palladium(II). The reaction mixture was heated at 100° C. for 3 h then cooled to room temperature. Diethyl ether followed by 150 mL of aqueous potassium fluoride (25 g) solution were added and the mixture stirred at room temperature for 1 h then filtered through Celite. The organic phase was separated and the aqueous phase re-extracted three times with diethyl ether. The combined organic phase was washed three times with water, twice with saturated aqueous sodium bicarbonate solution, brine, dried over magnesium sulfate and the solvent removed in vacuo. Trituration with hexanes afforded 3.71 g of the vinyl ether as a tan solid.

To a solution of 2.00 g (0.0108 mol) of the vinyl ether in 24 mL of THF and 8 mL of water at 0° C. was added 1.93 g (0.0108 mol) of N-bromosuccinimide. The solution was stirred at 0° C. for 40 min. Water was added and the mixture extracted with diethyl ether. The organic phase was washed with saturated aqueous sodium bicarbonate solution, brine, dried over magnesium sulfate, and the solvent removed in vacuo. Biotage chromatography (40M column, 25, 30% diethyl ether-hexanes) afforded 1.63 g (64%) of the title compound as a white solid: $^1$H NMR (400 MHz, CDCl$_3$) δ 8.17 (m, 1H), 7.74 (m, 1H), 4.95 (d, J=0.6 Hz, 2H).

Step B. 6-Chloropyridazin-3-yloxirane.

Following the procedure outlined in Example 1, Step B the title compound was prepared from 3-(2-bromoacetyl)-6-chloropyridazine: NMR (400 MHz, CDCl$_3$) δ 7.53 (d, J=8.8 Hz, 1H), 7.29 (d, J=9.0 Hz, 1H), 4.36 (dd, J=4.1, 2.5 Hz, 1H), 3.32 (dd, J=5.1, 4.3 Hz, 1H), 2.89 (dd, J=5.1, 2.4 Hz, 1H).

Step C. (R)-N-[2-(4-Nitrophenyl)ethyl]-2-hydroxy-2-(6-chloro-3-pyridazinyl)ethylcarbamic acid 1,1-dimethylethyl ester.

To a solution of 310 mg (1.98 mmol) of 6-chloropyridazin-3-yloxirane in 5 mL of acetonitrile under an atmosphere of nitrogen was added 632 mg (5.94 mmol) of lithium perchlorate. After stirring for 5 min 362 mg (2.16 mmol) of p-nitrophenethylamine was added and the solution stirred at room temperature overnight. The solvent was removed in vacuo and the residue partitioned between water and ethyl acetate. The organic phase was separated and the aqueous phase re-extracted with ethyl acetate. The combined organic phase was washed with brine, dried over magnesium sulfate and the solvent removed in vacuo to leave the resultant ethanolamine.

To a solution of the ethanolamine in 8 mL of dichloromethane was added 518 mg (2.37 mmol) of di-tert-butyldicarbonate followed by 10 ml of THF. The solution was stirred at room temperature for 2 h then the solvent removed in vacuo. Biotage chromatography (40S column, 40% ethyl acetate-hexanes) afforded 630 mg (75%) of the title compound as a foam.

Step D. (R)-N-[2-(4-aminophenyl)ethyl]-2-hydroxy-2-(3-pyridazinyl)ethylcarbamic acid 1,1-dimethylethyl ester.

To a solution of 630 mg (1.49 mmol) of (R)-N-[2-(4-nitrophenyl)ethyl]-2-hydroxy-2-(6-chloro-3-pyridazinyl)ethylcarbamic acid 1,1-dimethylethyl ester in 15 mL of methanol under an atmosphere of nitrogen was added 126 mg of 20 wt % palladium hydroxide on carbon followed by 0.90 mL of 5N aqueous sodium hydroxide solution. The mixture was purged three times with hydrogen then subjected to a balloon of hydrogen for 1.5 h. The catalyst was filtered off through Celite and the filtrate evaporated in vacuo The residue was pre-absorbed on florisil. Biotage chromatography (40S column, 3% methanol-dichloromethane) afforded 250 mg (47%) of the title compound as a colorless oil: NMR (400 MHz, CDCl$_3$) δ 9.10 (d, J=3.9 Hz, 1H), 7.81 (d, J=8.4 Hz, 1H), 7.51 (dd, J=8.4, 4.9 Hz 1H), 6.94 (d, J=7.6 Hz, 2H), 6.67 (d, J=8.0 Hz, 2H), 5.22 (s, 1H), 3.72 (m, 2H), 3.36 (m, 1H), 3.24 (m, 1H), 2.68 (m, 2H), 1.46 (s, 9H).

Step E. (R)-N-[4-[2-[[2-Hydroxy-2-(3-pyridazinyl)ethyl]amino]ethyl]phenyl]-2-(2-amino-4-thiazolyl)acetamide.

Following the procedure outlined in Example 1 Step E, the title compound was prepared from (R)-N-[2-(4-aminophenyl)ethyl]-2-hydroxy-2-(3-pyridazinyl)ethylcarbamic acid 1,1-dimethylethyl ester. NMR (400 MHz, CD$_3$OD) δ 9.09 (dd, 1H, J=1.7, 5.0 Hz), 7.87 (dd, 1H, J=1.7, 8.5 Hz), 7.73 (dd, 1H, J=4.9, 8.6 Hz), 7.50 (overlapping d, 2H), 7.18 (overlapping d, 2H), 6.35 (d, 1H, J=0.8 Hz), 5.11 (dd, 1H, J=4.0, 8.5Hz), 3.56 (d, 2H, J=0.7 Hz), 3.19 (dd, 1H, J=3.9, 12.5 Hz), 3.07–2.97 (m, 3H), 2.84 (br t, 2H, J=7.4 Hz).

EXAMPLE 4

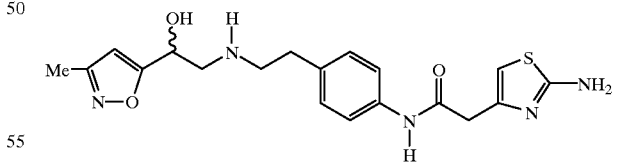

(R)-N-[4-[2-[[2-Hydroxy-2-(2-methyl-5-isoxazolyl)ethyl]amino]ethyl]phenyl]-2-(2-amine-4-thiazolyl)acetamide.

Following the procedure outlined in Example 1 Step E, the title compound was prepared from N-[2-[4-(aminophenyl)]ethyl]-2-hydroxy-2-(3-methylisoxazol-5-yl) ethylcarbamic acid 1,1-dimethylethyl ester (Fisher et al., U.S. Pat. No. 5,705,515) and 2-amino-4-thiazolylacetic acid: NMR (CD$_3$OD) δ 7.49, (d, J=8.6 Hz, 2H), 7.16, (d, J=8.4 Hz, 2H), 6.35, (s, 1H), 6.16, (s, 1H), 4.86–4.84, (m, 1H), 3.55, (s, 2H), 2.94–2.77, (m, 6H), 2.24, (s, 3H).

EXAMPLE 5

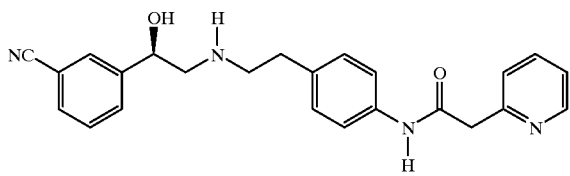

(R)-N-[4-[2-[[2-Hydroxy-2-(3-cyanophenyl)ethyl]amino] ethyl]phenyl]-2-(2-pyridyl)acetamide.

Following the procedure outlined in Example 1 Step E, the title compound was prepared from N-[2-[4-(aminophenyl)]ethyl]-2-hydroxy-2-(3-cyanophenyl) ethylcarbamic acid 1,1-dimethylethyl ester (Fisher et al., U.S. Pat. No. 5,561,142) and 2-pyridylacetic acid: NMR (CD$_3$OD) δ 8.50–8.48, (m, 1H), 7.81, (dt, J=1.8, 7.8 Hz, 1H), 7.64, (br, 1H, 7.61–7.58, (m, 2H), 7.49, (d, J=8.4 Hz, 2H), 7.45, (d, J=8.2 Hz, 2H), 7.64–7.30, (m, 1H), 7.15, (d, J=8.6 Hz, 2H), 4.79, (dd, J=4.5, 8.2 Hz, 1H), 3.90, (s, 2H), 2.91–2.71, (m, 6H).

EXAMPLE 6

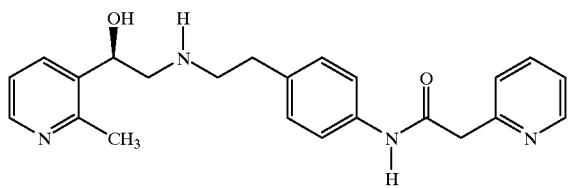

(R)-N-[4-[2-[[2-Hydroxy2-(3-cyanopbenyl)ethyl]amino] ethyl]phenyl]-2-(2-amino-4-thiazolyl)acetamide.

Following the procedure outlined in Example 1 Step E, the title compound was prepared from N-[2-[4-(aminophenyl)]ethyl]-2-hydroxy-2-(3-cyanophenyl) ethylcarbamic acid 1,1-dimethylethyl ester (Fisher et al., U.S. Pat. No. 5,561,142) and 2-amino-4-thiazolylacetic acid. NMR (CD$_3$OD) δ 7.70, (br, 1H), 7.64–7.59, (m, 2H), 7.50–7.46, (m, 3H), 7.15, (d, J=8.6 Hz, 2H), 6.35, (s, 1H), 4.79, (dd, J=4.5, 8.2 Hz), 1H), 3.56, (s, 2H), 2.89–2.74, (m, 6H).

EXAMPLE 7

Step A. 3-Acetyl-2-methylpyridine.

To a suspension of 5.0 g (36.5 mmol) of 2-methylnicotinic acid in 100 mL of dry THF cooled to 0° C., methyl lithium (1.5 M in ethyl ether) was added over ten min, yielding a yellow-orange mixture. After stirring for an additional 2 h at 0° C., 6.95 mL (54.8 mmol) of trimethylsilyl chloride was added rapidly. The reaction mixture was allowed to warm to room temperature and stir overnight. The resultant clear yellow solution was then quenched with 1 N aqueous hydrochloric acid (150 mL) and stirred for 0.5 h. The aqueous layer was then separated and brought to pH 8.0 using solid sodium bicarbonate. After extraction of the aqueous phase with ethyl ether (6×100 mL), the combined ethyl ether extracts were washed with brine and dried over sodium sulfate. Filtration and removal of solvent in vacuo yielded an amber oil which was purified by flash chromatography (30→50% ethyl acetate/hexanes) on silica gel to yield 2.25 g of a yellow oil, 46% yield. The $^1$H NMR spectra of this compound appears as a rotameric mixture: $^1$H NMR (CDCl$_3$) δ: 9.04, (d, J=2.1 Hz, 1H), 8.14, (d, J=2.3 Hz, 1H), 8.11, (d, J=Hz, 1H), 2.62, (m, 1H).

Step B. 3-Chloroacetyl-2-methylpyridine hydrochloride.

To 2.25 g (16.6 mmol) of the ketone from Step A dissolved in 20 mL of ethyl ether was added 20 mL of 1.0 M hydrogen chloride in ethyl ether, resulting in a pale yellow slurry. After 30 min, the precipitate was filtered and washed with ethyl ether. After drying in vacuo, 2.80 g (16.3 mmol) of a pale yellow powder was obtained. This material was dissolved in 15 mL of a solution of 1.0 M hydrogen chloride in acetic acid and treated with 2.18 g (16.3 mmol) of N-chlorosuccinimide. After six days, the reaction mixture was concentrated in vacuo, and the resultant pale yellow residue solidified on standing. This material was triturated with 20% acetic acid/ethyl ether, (3×50 mL) to afford 2.62 g of a white powder, 77% yield. The $^1$H NMR spectra of this compound appears as a rotameric mixture (65:35, rotamer A: rotamer B): $^1$H NMR (CDCl$_3$) δ: 9.16, (d, J=2.0 Hz, 1H, rotamer A), 8.84, (dd, J=2.0, 8.4 Hz, 1H, rotamer A), 8.64, (d, J=2.0 Hz, 1H, rotamer B), 8.50, (dd, J=2.0, 8.4 Hz, 1H, rotamer B), 7.96, (d, J=8.4 Hz, 1H, rotamer A), 7.86, (d, J=8.4 Hz, 1H, rotamer B), 4.93, (s 1H, rotamer A), 3.74, (2d, J=11.8 Hz, 2H, rotamer B), 2.77, (s 1H, rotamer A), 2.72, (s 1H, rotamer B).

Step C. (R)-N-[2-(4-Nitrophenyl)ethyl]-2-hydroxy-2-(2-methyl-3-pyridyl)ethylcarbamic acid 1,1-methylethyl ester.

The title compound was prepared from the chloroketone from Step B following the procedure outlined in Example 1, Steps B and C.

Step D. (R)-N-[2-(4-Aminophenyl)ethyl]-2-hydroxy-2-(2-methyl-3-pyridyl)ethylcarbamic acid 1,1-dimethylethyl ester.

To a solution of 705 mg (1.90 mmol) of (R)-N-[2-(4-nitrophenyl)ethyl]-2-hydroxy-2-(2-methyl-3-pyridyl) ethylcarbamic acid 1,1-dimethylethyl ester in 25 mL of methanol was added 141 mg of 20% palladium hydroxide on carbon and the mixture was allowed to stir for 2 h under 1 atm of hydrogen. The reaction mixture was filtered through a pad of Celite and concentrated in vacuo. Purification by flash chromatography (2→4% MeOH/CH$_2$Cl$_2$/1% NH$_{40}$OH) on silica gel afforded 509 mg of a white foam, 78% yield: $^1$H NMR (CDCl$_3$) δ: 8.3, (d, J=3.9 Hz, 1H, 7.57, (d, J=7.5 Hz, 1H), 7.10, (d, J=8.1Hz, 1H), 6.87, (d, J=7.0 Hz, 2H), 6.59, (d, J=8.4 Hz, 2H), 4.85–4.80, (m, 1H), 4.65, (br, 1H), 3.60–3.05, (m, 6H), 2.65–2.55, (m, 2H), 2.52, (s, 311), 1.45, (s, 9H).

Step E. (R)-N-[4-[2-[[2 Hydroxy-2-(2-methyl-3pyridyl) ethyl]amino]ethyl]phenyl]-2-(2-amino4-thiazolyl) acetamide.

Following the procedure outlined in Example 1 Step E, the title compound was prepared from N-[2-(4-aminophenyl)ethyl]-2-hydroxy-2-(2-methyl-3-pyridyl) ethylcarbamic acid 1,1-dimethylethyl ester and 2-(2-pyridyl)acetic acid: NMR (CD$_3$OD) δ 8.50–8.48, (m, 1H), 8.37, (d, J=2.1 Hz, 1H), 7.81, (dt, J=1.8, 7.7 Hz, 1H), 7.69, (dd, J=2.1, 8.0 Hz, 1H), 7.49, (d, J=8.6 Hz, 2H), 7.45, (d, J=7.8 Hz, 1H), 7.34–7.31, (m, 1H), 7.25, (d, J=8.2 Hz, 1H), 7.16, (d, J=8.4 Hz, 1H), 4.78, (dd, J=5.5,7.4 Hz, 1H), 3.89, (s, 2H), 2.91–2.77, (m, 6H), 2.49, (s, 3H).

EXAMPLE 8

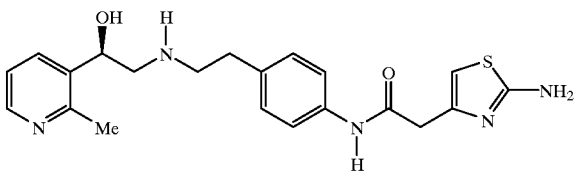

(R)-N-[4-[2-[[2-Hydroxy-2-(2-methyl-3-pyridyl)ethyl]amino]ethyl]phenyl]-2-(2-pyridyl)acetamide.

Following the procedure outlined in Example 7 the title compound was prepared from 2-amino4-thiazolylacetic acid: NMR (CD$_3$OD) δ 8.38, (d, J=2.2 Hz, 1H, 7.69, (dd, J=2.4, 8.0 Hz, 1H), 7.49, (d, J=8.4 Hz, 2H), 7.26, (d, J=8.0 Hz, 1H), 7.16, (d, J=8.4 Hz, 2H), 6.35, (s, 1H), 4.82–4.78, (m, 1H), 3.55, (s, 2H), 2.93–2.78, (m, 6H), 2.50, (s, 3H).

EXAMPLE 9

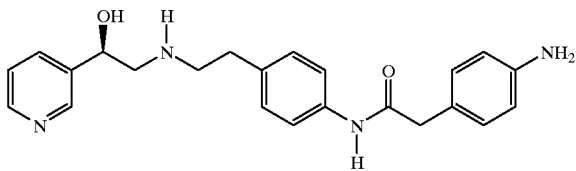

(R)-N-[4-[2-[[2-Hydroxy-2-(3-pyridyl)ethyl]amino]ethyl]phenyl]-2-(4-aminophenyl)acetamide.

A solution of N-[2-(4-aminophenyl)ethyl]-2-hydroxy-2-(3-pyridyl)ethylcarbamic acid 1,1-dimethylethyl ester (Fisher et al., U.S. Pat. No. 5,561,142; 321 mg, 0.90 mmol) in 5 mL of dichloromethane was cooled in ice-water and treated sequentially with pyridine (0.090 mL, 1.1 mmol) and 4-nitrophenylacetyl chloride (200 mg, 1.00 mmol). After 2 h, the volatiles were removed in vacuo, and the residue was purified by flash chromatography on silica gel (5% methanol in dichloromethane eluant) to afford the BOC intermediate (460 mg). A 350-mg portion was dissolved in 6 mL of methanol, treated with 50 mg of 10% palladium on carbon catalyst, and the mixture was stirred under 1 atm of hydrogen for 18 h. Filtration through a pad of Celite afforded 338 mg of off-white foam. A 40-mg sample was treated with 4 mL of 1:1 trifluoroacetic acid/dichloromethane at room temperature for 60 min. The solvent was removed in vacuo and the residue was purified by preparative TLC (1 mm silica gel; 7:1 dichloromethane: 10% ammonium hydroxide in methanol eluant) to afford 36 mg of a beige powder: NMR (CD$_3$OD) δ 8.51 (1H, d, J=1.6 Hz), 8.41 (1H, dd, J=4.9, 1.6 Hz), 7.81 (1H, d, J=7.6 Hz), 7.45 (2H, d, J=7.8 Hz), 7.38 (1H, dd, J=7.6,4.9 Hz), 7.14 (2H, d, J=7.8 Hz), 7.09 (2H, d, J=8.4 Hz), 6.71 (2H, d, J=8.4 Hz), 4.81 (1H, apparent t, J=6.3 Hz), 3.51 (2H, s), 2.75–2.95 (6H, m); EIMS, m/e 391.3 (M+H).

EXAMPLE 10

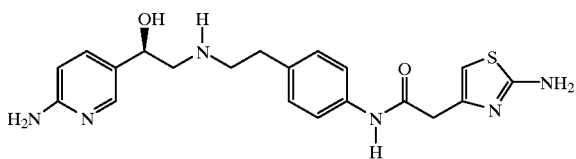

(R)-N-[4-[2-[[2-Hydroxy-2-(6-amino3-pyridyl)ethyl]amino]ethyl]phenyl]-2-(2-amino-4-thiazolyl)acetamide.

Following the procedure outlined in Example 1 Step E, the title compound was prepared from (R)-N-[2-(4-aminophenyl)ethyl]-2-hydroxy-2-(tetrazolo[1,5-a]pyrid-6-yl)ethylcarbamic acid 1,1-dimethylethyl ester (Fisher et al., U.S. Pat. No. 5,561,142) with the exception that hydrolysis of the tetrazine was effected by treatment with tin(II) chloride in methanol at 60 ° C. overnight. Deprotection of the resultant Boc intermediate was as outlined in Example 1: $^1$H NMR (400 MHz, CD$_3$OD) δ 7.83 (d, 1H, J=2.2 Hz), 7.47 (d, 2H, J=8.4 Hz), 7.42 (dd, 1H, J=8.7, 2.5 Hz), 7.14 (d, 2H, J=8.6 Hz), 6.54 (d, 1H, J=8.8 Hz), 6.35 (s, 1H), 4.60 (m, 1H), 3.55 (s, 2H), 2.88–2.70 (m, 6H).

EXAMPLE 11

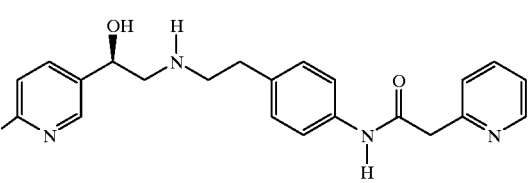

(R)-N-[4-[2-[[2-Hydroxy-2-(6-amino-3-pyridyl)ethyl]amino]ethyl]-phenyl]-2-(2-pyridyl)acetamide.

Following the procedure outlined in Example 10 the title compound was prepared from 2-pyridylacetic acid: $^1$H NMR (400 Mz, CD$_3$OD) δ 8.49 (d, 1H, J=4.3 Hz), 7.83–7.79 (m, 2H), 7.81–7.41 (m, 5H), 7.15 (d, 2H, J=8.4 Hz), 6.54 (d, 1H, J=8.6 Hz), 4.60 (m, 1H), 3.89 (s, 2H), 2.89–2.69 (m, 6H).

EXAMPLE 12

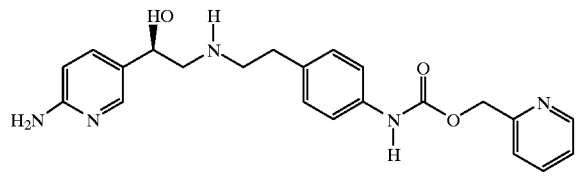

(R)-N-[4-[2-[[2-Hydroxy-2-(6-amino-3-pyridylmethyl)ethyl]amino]ethyl]phenyl]carbamic acid 2-pyridylmethyl ester.

To a solution of 100 mg (0.25 mmol) of (R)-N-[2-(4-aminophenyl)ethyl]-2-hydroxy-2-(tetrazolo[1,5a]-pyrid-6-yl)ethylcarbamic acid 1,1-dimethylethyl ester (Fisher et al., U.S. Pat. No. 5,561,142) in 3 mL of toluene was added 0.15 mL (0.3 mmol) of a 20% solution of phosgene in toluene. The reaction was stirred at 100° C. for 40 min before the addition of 0.029 mL (0.3 mmol) of 2-(hydroxymethyl) pyridine and 0.030 mL (0.214 mmol) of triethylamine. The reaction was maintained at 100° C. for 16 h, and then cooled, concentrated in vacuo, and the residue purified twice by preparative TLC (silica gel, 1% methanol/dichloromethane then 10% methanol/ethyl acetate) to afford 24 mg of coupled material. Removal of the two protecting groups was performed as in Example 10 followed by purification by preparative TLC (silica gel, 9/1/90 methanol/ammonium hydroxide/dichloromethane) and then reverse phase preparative HPLC (30/70 methanol/water containing 0.1% trifluoroacetic acid) to yield 13 mg of the title compound as its tris TFA salt: $^1$H NMR (400 MHz, CD$_3$OD) δ 8.7 (d, 1H, J=4 Hz), 8.23 (t, 1H, J =7 Hz), 7.98 (dd, 1H, J=10, 2 Hz), 7.88–7.81 (m, 2H), 7.7 (m, 1H), 7.42 (d, 2H, J=8 Hz), 7.2 (d, 2H, J=8 Hz), 7.03 (d, 1H, J=10 Hz), 5.39 (s, 2H), 4.98–4.92 (m, 1H), 3.3–3.18 (m, 4H), 3.02–2.93 (m, 2H).

What is claimed is:

1. A compound having the formula I:

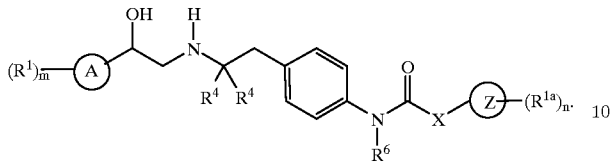

wherein m is 0 to 5;
n is 0 to 5;
p is 0, 1 or 2;

A is
- (1) benzene,
- (2) a 5 or 6-membered heterocyclic ring with from 1 to 4 heteroatoms selected from oxygen, sulfur and nitrogen,
- (3) a benzene ring fused to a 5 or 6-membered heterocyclic ring with from 1 to 4 heteroatoms selected from oxygen, sulfur and nitrogen, or
- (4) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen;

X is
- (1) $C_1-C_3$ alkylene,
- (2) $C_1-C_3$ alkylene wherein said alkylene contains Q,
- (3) $NR^6$,
- (4) O, or
- (5) a bond;
  with the proviso that when $R^6$ is H, Z is heteroaryl and X is $C_1-C_3$ alkylene, NH, or a bond, the moiety $(R^1)m-A$ is not phenyl, pyridyl, phenyl monosubstituted with halogen or pyridyl monosubstituted with halogen; with the further proviso that when Z is pyridyl, oxazolyl, thiazolyl or imidazolyl, X is methylene, and A is phenyl, then $R^1$ attached to A is not hydroxy;

Z is
- (1) phenyl,
- (2) naphthyl,
- (3) a 5 or 6-membered heterocyclic ring with from 1 to 4 heteroatoms selected from oxygen, sulfur and nitrogen,
- (4) a benzene ring fused to a $C_5-C_{10}$ carbocyclic ring,
- (5) a benzene ring fused to a 5 or 6-membered heterocyclic ring with from 1 to 4 heteroatoms selected from oxygen, sulfur and nitrogen,
- (6) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen, or
- (7) a 5 or 6-membered heterocyclic ring with from 1 to 4 heteroatoms selected from oxygen, sulfur and nitrogen fused to a $C_5-C_{10}$ carbocyclic ring;

$R^1$ is
- (1) $C_1-C_{10}$ alkyl optionally substituted with up to 5 groups selected from
  - (a) hydroxy,
  - (b) halogen,
  - (c) cyano,
  - (d) $QR^2$,
  - (e) $C_3-C_8$ cycloalkyl,
  - (f) Z optionally substituted with up to 5 groups selected from halogen, $R^2$, $QR^2$, oxo, and $CO_2R^2$
  - (g) $Q'COR^3$,
  - (h) $S(O)_pNR^2R^2$,
  - (i) $NR^2SO_2R^3$, and
  - (j) $Q'CO_2R^2$;
- (2) $C_3-C_8$ cycloalkyl,
- (3) oxo,
- (4) halogen,
- (5) cyano,
- (6) $QR^2$, (7) $S(O)_pNR^2R^2$,
- (8) $Q'COR^3$,
- (9) $NR^2SO_2R^3$,
- (10) $Q'CO_2R^2$, or
- (11) Z optionally substituted with up to 5 groups independently selected from
  - (a) $R^2$,
  - (b) $QR^2$,
  - (c) halogen, and
  - (d) oxo;

$R^{1a}$ is
- (1) a group selected from $R^1$, or
- (2) Z optionally substituted with up to 5 groups selected from $R^1$;

$R^2$ is
- (1) hydrogen,
- (2) $C_1-C_{10}$ alkyl optionally substituted with up to 5 groups selected from
  - (a) hydroxy,
  - (b) halogen,
  - (c) $CO_2R^4$,
  - (d) $S(O)_p-C_1-C_{10}$ alkyl,
  - (e) $C_3-C_8$ cycloalkyl,
  - (f) $C_1-C_{10}$ alkoxy optionally substituted with up to 5 halogens, and
  - (g) Z optionally substituted with up to 5 groups selected from halogen, trifluoromethyl, trifluoromethoxy, $C_1-C_{10}$ alkyl and $C_1-C_{10}$ alkoxy,
- (3) $C_3-C_8$ cycloalkyl, or
- (4) Z optionally substituted with up to 5 groups selected from
  - (a) halogen,
  - (b) nitro,
  - (c) oxo,
  - (d) $NR^4R^4$,
  - (e) $C_1-C_{10}$ alkoxy optionally substituted with up to 5 halogens,
  - (f) $S(O)_p-C_1-C_{10}$ alkyl, and
  - (g) $C_1-C_{10}$ alkyl optionally substituted with up to 5 groups selected from hydroxy, halogen, trifluoromethyl, cyano, $CO_2R^4$, $C_3-C_8$ cycloalkyl, and $QR^5$;

$R^3$ is
- (1) $R^2$ or
- (2) $NR^2R^2$;

$R^4$ is
- (1) H, or
- (2) $C_1-C_{10}$ alkyl;

$R^5$ is
- (1) Z optionally substituted with up to 5 groups selected from halogen, trifluoromethyl, cyano, $C_1-C_{10}$ alkyl and $C_1-C_{10}$ alkoxy, or (2) $C_1$–$C_{10}$ alkyl;

$R^6$ is
(1) H or
(3) $C_1$–$C_{10}$ alkyl, or
when X is $NR^6$ the two $R^6$ groups together complete a 5- or 6-membered ring;

Q is
(1) $N(R^2)$,
(2) O or
(3) $S(O)_p$;

Q' is
(1) $NR^2$),
(2) Q or
(3) a bond; or a pharmaceutically acceptable salt thereof.

2. A compound of claim 1 wherein

A is
(1) a 5- or 6-membered heterocyclic ring with from 1 to 4 heteroatoms selected from oxygen, sulfur and nitrogen, other than pyridyl,
(2) a benzene ring fused to a 5 or 6-membered heterocyclic ring with from 1 to 4 heteroatoms selected from oxygen, sulfur and nitrogen, or
(4) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen.

3. A compound of claim 1 wherein
$R^4$ and $R^6$ are each hydrogen.

4. A compound of claim 1 having the formula Ia:

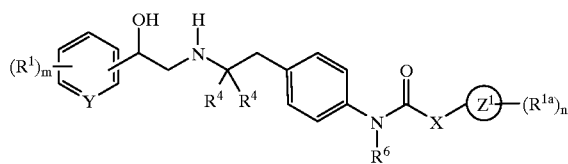

Ia wherein
m is 0 or 1;
Y is CH or N;
$R^1$ is halogen;
$Z^1$ is
(1) phenyl,
(2) naphthyl,
(5) a benzene ring fused to a $C_5$–$C_{10}$ carbocyclic ring.

5. A compound of claim 1 having the formula Ib:

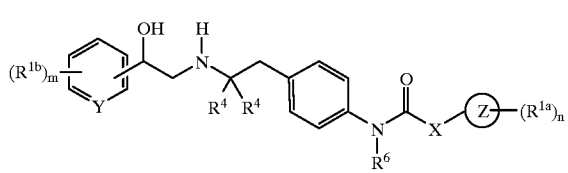

Ib wherein
m is 1 to 3;
Y is CH or N;
$R^{1b}$ is
(1) $C_1$–$C_{10}$ allyl optionally substituted with up to 5 groups selected from (a) hydroxy,
(b) halogen,
(c) cyano,
(d) $QR^2$,
(e) $C_3$–$C_8$ cycloalkyl,
(f) Z optionally substituted with up to 5 groups selected from halogen, $R^2$, $QR^2$, oxo, and $CO_2R^2$
(g) $Q'COR^3$,
(h) $S(O)_pNR^2R^2$,
(i) $NR^2SO_2R^3$, and
(j) $Q'CO_2R^2$;
(2) $C_3$–$C_8$ cycloalkyl,
(3) cyano,
(4) $QR^2$,
(5) $S(O)_pNR^2R^2$,
(6) $Q'COR^3$,
(7) $NR^2SO_2R^3$,
(8) $Q'CO_2R^2$, or
(9) Z optionally substituted with up to 5 groups independently selected from
(a) $R^2$,
(b) $QR^2$,
(c) halogen, and
(e) oxo.

6. A compound of claim 5 wherein
m is 1, and
$R^{1b}$ is cyano or $QR^2$.

7. A compound of claim 5 wherein
m is 1,
$R^{1b}$ is cyano or amino, and
Z is selected from the group selected from phenyl, pyridyl and thiazolyl.

8. A compound of claim 1 having the formula Ic:

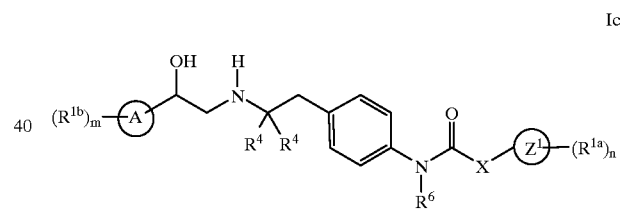

Ic wherein
$Z^1$ is
(1) phenyl,
(2) naphthyl,
(6) a benzene ring fused to a $C_5$–$C_{10}$ carbocyclic ring.

9. A compound of claim 1 selected from the group consisting of:

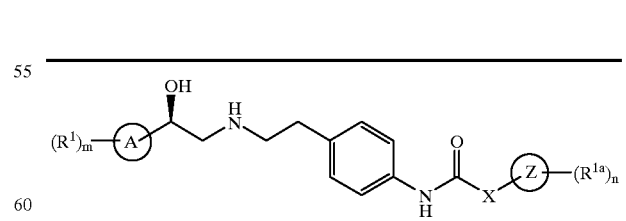

| $(R^1)_m$—A | X—Z—$(R^{1a})_n$ |
|---|---|
| 6-cyano-2-pyridyl | 2-amino-4-thiazolylmethyl |
| 6-cyano-2-pyridyl | 2-pyridylmethyl |
| 3-pyridazinyl | 2-amino-4-thiazolylmethyl |
| 3-methyl-5-isoxazolyl | 2-amino-4-thiazolylmethyl |

-continued

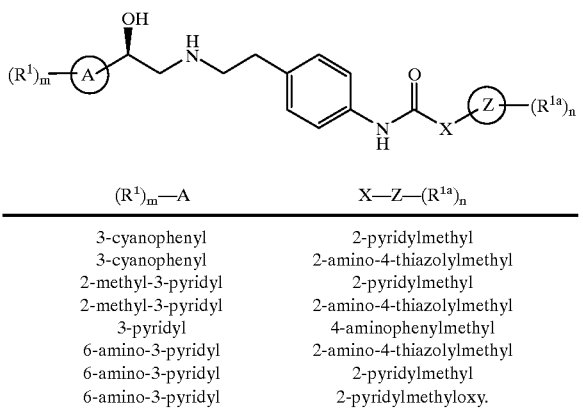

| (R¹)ₘ—A | X—Z—(R¹ᵃ)ₙ |
|---|---|
| 3-cyanophenyl | 2-pyridylmethyl |
| 3-cyanophenyl | 2-amino-4-thiazolylmethyl |
| 2-methyl-3-pyridyl | 2-pyridylmethyl |
| 2-methyl-3-pyridyl | 2-amino-4-thiazolylmethyl |
| 3-pyridyl | 4-aminophenylmethyl |
| 6-amino-3-pyridyl | 2-amino-4-thiazolylmethyl |
| 6-amino-3-pyridyl | 2-pyridylmethyl |
| 6-amino-3-pyridyl | 2-pyridylmethyloxy. |

10. A compound of claim 1 wherein the carbon atom attached to ring A has the R configuration.

11. A method for the treatment of diabetes which comprises administering to a diabetic patient an effective amount of a compound of claim 1.

12. A method for the treatment of obesity which comprises administering to an obese patient an effective amount of a compound of claim 1.

13. A method for lowering triglyceride levels and cholesterol levels or raising high density lipoprotein levels which comprises administering to a patient needing lower triglyceride and cholesterol levels or higher high density lipoprotein levels an effective amount of a compound of claim 1.

14. A method for decreasing gut motility which comprises administering to a patient in need of decreased gut motility, an effective amount of a compound of claim 1.

15. A method for reducing neurogenic inflammation of airways which comprises administering to a patient in need of reduced neurogenic inflammation, an effective amount of a compound of claim 1.

16. A method for reducing depression which comprises administering to a depressed patient an effective amount of a compound of claim 1.

17. A method for treating gastrointestinal disorders which comprises administering to a patient with gastrointestinal disorders an effective amount of a compound of claim 1.

18. A pharmaceutical composition which comprises an inert carrier and a therapeutically effective amount of a compound of claim 1.

* * * * *